(12) United States Patent
Schaufler (10) Patent No.: US 7,098,315 B2
(45) Date of Patent: Aug. 29, 2006

(54) METHOD OF PREPARING A COLLAGEN SPONGE, A DEVICE FOR EXTRACTING A PART OF A COLLAGEN FOAM, AND AN ELONGATED COLLAGEN SPONGE

(75) Inventor: Alfred Schaufler, Puchenau (AT)

(73) Assignee: Nycomed Pharma AS, Asker (NO)

( * ) Notice: Subject to any disclaimer, the term of this patent is extended or adjusted under 35 U.S.C. 154(b) by 261 days.

(21) Appl. No.: 10/054,854

(22) Filed: Jan. 25, 2002

(65) Prior Publication Data

US 2002/0153632 A1 Oct. 24, 2002

Related U.S. Application Data

(60) Provisional application No. 60/263,699, filed on Jan. 25, 2001.

(30) Foreign Application Priority Data

Jan. 25, 2001 (DK) ................ 2001 00135

(51) Int. Cl.
*A61K 38/17* (2006.01)
*C07K 14/00* (2006.01)

(52) U.S. Cl. ............ 530/356; 530/354; 530/355; 530/419; 530/424; 530/427

(58) Field of Classification Search ........ 530/356, 530/354, 355, 419, 423, 424, 427; 422/161; 514/2
See application file for complete search history.

(56) References Cited

U.S. PATENT DOCUMENTS

| | | | |
|---|---|---|---|
| 4,453,939 A | 6/1984 | Zimmerman et al. | |
| 4,606,337 A | 8/1986 | Zimmermann et al. | |
| 4,626,286 A | 12/1986 | Lubbs | |
| 5,019,087 A | 5/1991 | Nichols | |
| 5,618,551 A | 4/1997 | Tardy et al. | |
| 5,660,857 A | 8/1997 | Haynes et al. | |
| 5,942,278 A | 8/1999 | Hagedorn et al. | |
| 6,177,126 B1 | 1/2001 | Hagedorn et al. | |
| 6,733,774 B1 * | 5/2004 | Stimmeder .......... | 424/443 |

FOREIGN PATENT DOCUMENTS

| | | |
|---|---|---|
| EP | 0059265 | 9/1982 |
| EP | 0217917 B1 | 4/1987 |
| EP | 0578823 A1 | 1/1994 |
| EP | 0664132 A1 | 7/1995 |
| EP | 0664132 B1 | 7/1995 |
| FR | 2668936 | 5/1992 |
| GB | 1292326 | 10/1972 |
| JP | 7-59812 | 3/1995 |
| WO | 86/05811 | 10/1986 |
| WO | 93/19805 | 10/1993 |
| WO | 94/21739 | 9/1994 |
| WO | 96/40033 | 12/1996 |
| WO | 97/28832 | 8/1997 |
| WO | 97/37694 | 10/1997 |
| WO | 99/13902 | 3/1999 |
| WO | 99/56797 | 11/1999 |
| WO | 99/59647 | 11/1999 |

OTHER PUBLICATIONS

Patent Abstracts of Japan, vol. 1995, No. 6, Jul. 31, 1995 & JP 07 059812 A (Koken Co Ltd), Mar. 7, 1995, abstract & Database WPI, Week 199518, Derwent Publications Ltd., London, GB; An 1995-135943, abstract.

H. Osada et al., "Clinical Evaluation of a Haemostatic and Anti-adhesion Preparation Used to Prevent Post-surgical Adhesion", Journal of International Medical Research, vol. 27, No. 5, 1999, pp. 247-252, XP001085094, ISSN; 0300-0605, abstract.

Chemical Abstracts of "Microfibrillar and Microcrystalline Collagen I for Medicinal and Pharmaceutical Applications" Columbus, Ohio, U.S., vol. 98, Jun. 13, 1983, No. 24 (English translation).

Chemical Abstracts, Columbus, Ohio, U.S., vol. 98, Jun. 13, 1983, No. 24.

"Mechanisms in blood coagulation, fibrinolysis and the complement system", Cambridge University press 1991; Halkier, Torben: Chapter 5: Activation of prothrombin, pp. 54-70.

(Continued)

*Primary Examiner*—Jon Weber
*Assistant Examiner*—Abdel A. Mohamed
(74) *Attorney, Agent, or Firm*—Wenderoth, Lind & Ponack, L.L.P.

(57) ABSTRACT

A method of preparing a collagen sponge comprises mixing air into a collagen gel, so as to obtain a collagen foam which is dried. From the dried product thereby obtained, collagen sponge is obtained by isolating parts of sponge with a chamber diameter of more than 0.75 mm and less than 4 mm, or parts with an average chamber diagonal dimension of 3 mm. The collagen sponge may be used as a material for sealing wounds, possibly with a coating comprising a fibrin glue, such as a combination of fibrinogen, thrombin and aprotinin. A device for extracting a part of a collagen foam and for degenerating another part of the collagen foam to a collagen gel is disclosed. An elongated collagen sponge having a through-going hole or bore and a flexible wall may be used for re-establishing walls in a mammalian gastrointestinal funnel or trachea system.

38 Claims, 4 Drawing Sheets

OTHER PUBLICATIONS

"Mechanisms in blood coagulation, fibrinolysis and the complement system", Cambridge University press 1991; Halkier, Torben: Chapter 7: Formation and stabillisation of fibrin, pp. 80-103.

"Mechanisms in blood coagulation, fibrinolysis and the complement system", Cambridge University press 1991; Halkier, Torben: Chapter 24: Haemostasis, pp. 269-282.

* cited by examiner

| Process | Added material |

Step 1

Delivery of deep-frozen horse tendons

Storage of tendons at -18 °C to -25 °C
Controls: appearance, ash, degradability by collagenase

↓

Step 2

Peeling of horse tendons

Storage of peeled tendons
at -18 °C to -25 °C

↓

Step 3

Slicing of peeled horse tendons                  ← 70 % ethanol

Disinfection of tendons
with 70 % ethanol                                    ← water for injection or salt solution Washing of tendons with water or salt solution Deep-freezing Slicing

↓

Step 4

Washing and disinfection of tendon slices        ← water for injection or salt solution Washing with water or salt solution                  ← 70 % ethanol Disinfection with 70 % ethanol                       ← 0.45 % lactic acid in salt solution Washing with 0.45 % lactic acid in salt solution

METHOD OF PREPARING A COLLAGEN SPONGE, A DEVICE FOR EXTRACTING A PART OF A COLLAGEN FOAM, AND AN ELONGATED COLLAGEN SPONGE

The present application claims priority from Provisional Application Ser. No. 60/263,699, filed Jan. 25, 2001.

TECHNICAL FIELD

The present invention relates to a method of preparing a collagen sponge. The collagen sponge produced according to the invention is in particular useful in surgery primarily to stop capillary bleeding. The collagen sponge may also be used as a carrier to be coated with a fibrin glue preparation. The invention also relates to a device for extracting a part of a collagen foam. The invention further relates to an elongated collagen sponge, primarily for gastrointestinal use.

BACKGROUND OF THE INVENTION

Collagen has been used as a hemostyptic agent since the late sixties. Collagen is the most frequent structural protein in all mammalians. The monomeric protein of approximately 300 kDa (tropocollagen) is covalently crosslinked at specific sites. The mature protein is therefore insoluble and forms characteristic fibrils with high tensile strength. Numerous sub-classes of collagen have been described, the most common of which is collagen type I, the main collagen type in skin, tendons, bones and cornea. Collagen is a fibrous protein consisting substantially of a triple helix with a length of approximately 290 nm. Five of these triple helices (tropocollagen molecules) are staggered to form a microfibril with a diameter of approximately 3.6 nm. These microfibrils have polar and non-polar segments that are readily accessible for specific inter- and intrafibrillar interactions. Microfibrils are packed into a tetragonal lattice to form subfibrils with a diameter of about 30 nm. These subfibrils are then assembled into the collagen fibril, the basic unit of connective tissue, which has a diameter of several hundred nm and is therefore visible in a light microscope as a thin line, see reference 1. Collagen gel and collagen sponge, as produced during the manufacturing process, comprises these fibrils as the smallest units, as proved by microscopy.

Collagen may be used as a material for sealing wounds, possibly with a coating comprising a fibrin glue. Fibrin glues, i.e. the combination of fibrinogen, thrombin and aprotinin, have successfully been used therapeutically for many years for gluing tissues and nerves and for sealing surfaces when there is minor bleeding. One drawback of the fibrin glues has been that in case of major bleeding the glue is usually washed away before sufficient polymerization of fibrin has occurred. To overcome this problem surgeons have manually applied liquid fibrin glues to absorbable carriers such as collagen fleece.

Despite the impressive success of these combined applications this method has not been applied on a broad scale, due to some disadvantages. The preparation is relatively cumbersome, the method requires experience and skilled personnel, and the preparation is not readily available in cases of emergency, the time for preparation being in the range of 10 to 15 min. These factors stimulated the development of an improved product resulting in the development of a fixed combination of a collagen carrier covered with a coating of solid fibrinogen, solid thrombin and solid aprotinin as disclosed in EP 0 059 265. The product disclosed in EP 0 059 265, which has been marketed under the trademark TACHOCOMB®, is a hemostatic collagen sponge that can be applied directly to the wound. When the coating comes into contact with aqueous fluids like blood, other body fluids or saline, the components dissolve and fibrin is formed. The product is applied to the wound with a slight pressure and collagen is tightly bound (glued) to the injured surface. Hemostasis is achieved and the wound is sealed.

Beside some blood coagulation stimulating activity, the function of collagen in the hemostatic collagen sponge that TACHOCOMB® is mainly that of a carrier which adsorbs and confers mechanical stability to the coagulation preparation with which it is coated. Other advantages of collagen, in particular in the form of a sponge, are its biodegradability, its relatively high tensile strength, even in the wet state, its high resistance against the penetration of liquids and air, and its high flexibility in the wet state.

The present invention is primarily concerned with the production of a collagen sponge which may be used as a carrier for fibrinogen, thrombin and/or aprotinin, e.g., as in TACHOCOMB®. The collagen sponge may also be used directly, i.e. without a coating, as a bandage on topical injuries, for support of hemostasis, such as for prevention of rebleeding, for weak, diffuse bleeding from parenchymatic organs, for application on burns, skin grafts, decubitus or skin defects, or as a bandage on topical injuries.

In the prior art, a number of methods for preparing a collagen carrier have been suggested. WO 86/05811 discloses a weighted microsponge for immobilizing bioactive materials in motive bioreactor systems, the microsponge comprising a highly cross-linked collagen matrix. The highly cross-linked collagen matrix is prepared by milling a source of Type I, II or III collagen to yield fibers having a diameter on the order of 1 to 50 µm and a length no greater than 200 µm. The milled collagen is formed into a soluble collagen dissolved in a solvent, or an insoluble collagen dispersed in a solvent by admixture with a solvent, such as acetic acid, lactic acid, proprionic acid or butyric acid. In the case of a collagen dispersion, the mixing is accomplished with a high level of agitation using a blender, so as to produce microfibers of the collagen. Next, a weighting additive is blended with the collagen-liquid mixture and the composite mixture is formed into small droplets and solidified by freezing. A number of techniques for producing small particles are disclosed. The frozen composite is vacuum freeze-dried, the combination of freezing and drying being referred to as lyophilization. The freeze-dried collagen matrix composite is treated so as to cross-link the collagen. The collagen can be cross-linked using either chemical cross-linking agents, by severe dehydration at an elevated temperature or by a combination. The collagen matrix aimed at being resistant to collagenase and other enzymatic degradation thereby making these materials particularly suitable for culturing organisms. After washing the cross-linked collagen matrix, the microsponges may be sterilized and aseptically packaged. In the weighted microsponge, the collagen matrix has an open to the surface pore structure with an average pore size in the range of from about 1 to about 150 µm, the pores of the matrix occupying from about 70 to about 98% by volume of the microsponge. The microsponge further has an average particle size of from about 100 to about 1000 µm and a specific gravity of above about 1.05. The weighting material may be metal or alloys from metal, metal oxides and ceramics.

U.S. Pat. No. 5,660,857 discloses a process for preparing a composite comprising an insoluble protein matrix and an oleaginous material, which is useful as a material for surgical dressings and biomedical implants, and as a cosmetic material for application to the skin. The process of U.S. Pat. No. 5,660,857 comprises the steps of mixing a protein, the oleaginous material and water to form an emulsion of the oleaginous material in an aqueous dispersion of the protein, and subsequently drying or freeze-drying the emulsion to form a film or a sponge. The insoluble fibrous protein is predominantly comprised of insoluble collagen, which may suitably be obtained from bovine skin. In one embodiment, the collagen may be swollen in lactic acid prior to use.

WO 99/13902 discloses a method for producing a meningeal tissue growth matrix comprising the step of preparing physiologically compatible collagen which is substantially free of active viruses and prions. The collagen is formed into a film, a sponge, a non-woven collagen or a felt. The collagen is obtained by a process comprising cleaning skin, tendons, ligaments or bone of fat. The material is then subjected to an enzyme treatment, whereby the collagen material is swelled. The collagen material is then further swollen with an acid solution. The collagen mixture is then homogenized. The product obtained may be a matrix provided in the form of a collagen sponge, a non-woven matrix, felt or film, or a composite of two or more of the foregoing forms. A collagen sponge can be provided by adaptation of the methods for forming collagen sponges disclosed in U.S. Pat. No. 5,019,087. The sponge can be prepared by lyophilization of a collagen dispersion prepared according to WO 99/13902. The sponge density achieved is said to be about 0.1 mg/cm$^3$ to about 120 mg/cm$^3$. According to the disclosure of WO 99/13902, the pore size ranges from about 10 µm to about 500 µm. Laminate type of collagen sponge and collagen film are mentioned.

U.S. Pat. No. 5,618,551 relates to a non-crosslinked and potentially crosslinkable pepsintreated collagen or gelatin powder modified by oxidative cleavage in an aqueous solution, which is soluble at an acid pH and stable on storage at a temperature of below 0° C. for at least one month. The patent further relates to a process of preparing the powder, comprising preparing an acidic solution of pepsin-treated collagen, subjecting the acidic aqueous solution at room temperature to controlled oxidation, precipitating the oxidized and noncrosslinked pepsintreated collagen at an acid pH, and isolating, concentrating and dehydrating the non-crosslinked pepsintreated collaged so as to obtain it in the form of a reactive acidic powder, and freezing and storing the obtained reactive acidic powder at a temperature of below 0° C.

GB 1 292 326 discloses a method and apparatus for the preparation of collagen dispersions with a view to their applications, wherein a suspension of collagen fibers is prepared and subsequently introduced into a treatment chamber with stirring means. A sub-atmospheric pressure exists in the treatment chamber, in which the suspension is transformed into a dispersion by stirring and controlled acidification by means of a mineral or organic acid. According to the disclosure of GB 1 292 326, the preparation of spongy collagenic articles can be effected from dispersion or gels of collagen. In this context the documents refers to lyophilization and to dispersion or gels very rich in air bubbles. GB 1 292 326 further mentions a problem of controlling the introduction or the elimination of air bubbles in a satisfactory manner. The documents discloses, in two examples, a collagenic dispersion free of air bubbles with a collagen content of 2.5%, and an aerated dispersion of collagen with a collagen concentration of 2.5%, respectively.

Chemical Abstracts, Columbus Ohio, US, Vol. 98 13 Jun. 1983 No. 24 mentions a collagen obtained from animal tissues such as skin or tendon bone which has been submitted to acid treatment. The collagen is reaggregated by dialysis, during which process a net of highly birefringent crystal fibers is formed. The collagen can be shaped into 0.5 mm–2 cm sheets, or be mixed with air to form sponges, or be dispersed as a cream.

DESCRIPTION OF THE INVENTION

It has been found that the successful coating of a collagen sponge with a fibrin glue preparation depends on the texture of the collagen sponge. It is thus an object of the present invention to provide a method of producing a collagen sponge with a certain texture, in particular with the aim of making the collagen sponge suitable for coating with a fibrin glue preparation, so as to obtain a material for healing and sealing wounds. It is a further object of the invention to provide a method of producing a collagen sponge having improved physical characteristics in relation to prior art sponges, in the sense of improved humidity, elasticity, density and elasticity module. It is a further object of the invention to provide a method for preparing a collagen sponge which is air and liquid tight in the sense that, once the collagen sponge is applied to a wound, it will not allow air or liquid to soak through the collagen sponge. It is a still further object of the invention to provide a wound closing material which can be used in gastrointestinal funnels or trachea.

Thus, in a first aspect the invention provides a method of preparing a collagen sponge, comprising the steps of:
  preparing a collagen gel,
  mixing air into the collagen gel, so as to obtain a collagen foam,
  drying the collagen foam, so as to obtain a dry block of collagen sponge having chambers therein,
  isolating, from the block of collagen sponge, parts of sponge with a chamber diameter of more than 0.75 mm and less than 4 mm, or having a chamber diameter average of at most 3 mm.

In the present context, the term "chamber diameter" should be understood as the largest straight-line wall-to-wall distance in a chamber, i.e. as the largest diagonal straight-line distance of a chamber. The chambers may be of a polygonal shape, such as of an octagonal shape.

It has been found that a chamber diameter of more than 0.75 mm and less than 4 mm, or a chamber diameter average of at most 3 mm, renders the collagen sponge particularly useful for being coated with a fibrin glue preparation. Preferably, the collagen gel has a dry mass in the range of 2–20 mg dry mass per 1 g gel, such as 4–18 mg, such as 5–13 mg, such as 6–11 mg per 1 g gel. The dynamic viscosity of the collagen gel is preferably 2–20 N/cm, such as 4–10 N/cm, such as 6–8 N/cm. The collagen sponge preferably has a water content of not more than 20%, such as 10–15%, such as about 18%. The elasticity module of the collagen sponge is preferably in the range of 5–100 N/cm$^2$, such as 10–50 N/cm$^2$, and the density of the sponge is preferably 1–10 mg/cm$^3$, such as 2–7 mg/cm$^3$.

It has been found that a collagen sponge prepared by the method according to the invention is air and liquid tight in the sense that, once the collagen sponge is applied to a wound, it will not allow air or liquid to pass through the collagen sponge. Liquids are absorbed in the sponge. This effect is primarily achieved due to the fact that the step of mixing air into the collagen gel provides a collagen sponge which has a three-dimensional structure with stacked chambers separated and substantially totally enclosed by walls of collagen material, in contradiction to those known collagen sponges which have a fiber structure.

The collagen gel may comprise material of different types, such as type I, II or III from mammalian, transgenic or recombinant sources, but all other types of collagen can be used. The collagen may comprise material from tendons selected from the group consisting of equine tendons, human tendons, and bovine tendons. The collagen gel may additionally or alternatively comprise recombinant collagen material.

The collagen content of the isolated parts of sponge is preferably 50%–100% related to dry mass of the sponge, such as 75%–100%, such as 80%–100%, such as 85%–100%, such as 90%–100%, such as 92–100%, such as 92–98%, such as 93–97%, such as 94%–96%.

The step of preparing the collagen gel preferably comprises the steps of:
 storing the tendons at a temperature between −10° C. and −30° C., and peeling the tendons,
 removing foreign protein from the tendons,
 reducing germ content in the tendons,
 swelling the tendons,
 homogenizing the swelled tendons.

The steps of storing, peeling, removing protein, reducing of germ content, and swelling aim at purifying the raw material, whereas the step of homogenizing aims at obtaining the collagen in the form of a gel.

The step of reducing of germ content preferably comprises adding an acid, such as an organic acid such as lactic acid, to the tendons. Further, an organic solvent, such as an alcohol such as ethanol, is preferably added to the tendons. Further, the step of swelling of the tendons preferably comprises adding lactic acid to the tendons. The lactic acid used may be a 0.40–0.50% lactic acid, such as a 0.45% lactic acid.

The step of swelling of the tendons may comprise storing the tendons at a temperature of 4° C. to 25° C., such as a temperature of 10° C. to 20° C., for a period of 48 to 200 hours, such as a period of 100 to 200 hours.

The step of homogenizing the swelled tendons is preferably carried out so as to obtain a particle size of collagen gel fragments, i.e. fiber balls, with a diameter of 0.8–1.2 cm, such as approximately 1 cm. Further, the physical characteristics of the collagen gel are preferably as stated above. The appropriate characteristics may for example be achieved by performing the step of homogenizing the swelled tendons by means of a toothed disk mill or adequate homogenization equipment.

The step of mixing air into the collagen gel preferably comprises the steps of:
 mixing ambient air into the gel by means of a mixer so as to generate a collagen foam,
 feeding the mixed gel foam into a fractionizing channel, and
 separating collagen gel and collagen foam contained in the fractionizing channel.

At least some of the collagen gel separated from the collagen foam in the fractionizing channel may be led back to the mixer. In that case, the ratio between the amount of collagen gel which is led back to the mixer from the fractionizing channel and the amount of fresh collagen gel led to the mixer is preferably between 0.1 and 0.5. The step of separating collagen gel and collagen foam preferably comprises the steps of:
 separating a selected part of the collagen foam contained in the fractionizing channel, and
 leading the selected part of the collagen foam out of the fractionizing channel for drying thereof.

In a preferred embodiment of the method, a temperature of 15° C. to 40° C., such as 20° C. to 25° C., is maintained in the fractionizing channel.

Subsequent to mixing air into the collagen gel, the collagen foam may be homogenized for a period of 2 to 4 minutes.

Prior to the step of drying the collagen foam and subsequent to the step of mixing air into the collagen gel, a neutralizer may be added to the collagen foam, and the collagen foam is preferably neutralized in order to arrive from a pH-value of, usually, between 2.5 and 3.5 to a pH-value in the collagen foam between 6.5 and 8.5. A neutralizer comprising an ammonia solution may be used, and the collagen foam is preferably neutralized for a period of 5–30 hours, such as 10–20 hours, or such as approximately 24 hours.

Prior to the step of drying the collagen foam, the collagen foam is preferably filled into a drying container in such a way that substantially no air is drawn into the foam while filling.

The step of drying preferably comprises drying at a temperature between 15° C. and 60° C., such as between 20° and 40° C., for a period of 50–200 hours, such as 100–150 hours, so as to obtain a dry collagen sponge. The drying may be performed at a pressure slightly under atmospheric pressure, such as at a pressure between 700 and 900 mbar, such as approximately 800 mbar.

The collagen sponge produced by the method according to the invention preferably fulfils at least one of the following criteria:
 pH-value between 5.0 and 6.0,
 lactic acid content at the most 5%,
 ammonium content at the most 0.5%,
 soluble protein content, calculated as albumin content, at the most 0.5%,
 sulphate ashes content at the most 1.0%,
 heavy metal content at the most 20 ppm,
 microbiological purity, at the most $10^3$ CFU/g,
 collagen content of 75% to 100%,
 density of 1–10 mg/cm$^3$, such as 2–7 mg/cm$^3$,
 elasticity module of 5–100 N/cm$^2$, such as 10–50 N/cm$^2$.

The step of isolating parts of collagen sponge may comprise dividing the collagen sponge into a plurality of parts by cutting. The parts obtained may be shaped in any desirable form, such as conical, cylindrical, including cylindrical with an annular cross-section, rectangular, polygonal, cubic, and flat sheets or they may be transformed into a granulate by an appropriate granulating method etc.

In a second aspect, the present invention relates to a method of preparing a collagen sponge, comprising the steps of:
 preparing a collagen gel,
 mixing air into the collagen gel, so as to obtain a collagen foam,
 drying the collagen foam, so as to obtain a dry block of collagen sponge having chambers therein,
 isolating, from the block of collagen sponge, parts of sponge having the following properties:
 elasticity module in the range of 5 to 100 N/cm$^2$,
 density in the range of 1 to 10 mg/cm$^3$,
 chamber diameter of more than 0.75 mm and less than 4 mm, or a chamber diameter average of at most 3 mm.

It should be understood that any and all steps of the method according to the first aspect of the invention may also be performed in the method according to the second aspect of the invention. Further, any and all characteristics and features of the collagen sponge produced by the method according to the first aspect of the invention may also be achieved by the method according to the second aspect of the invention.

In a third aspect, the present invention provides a device for extracting a part of a collagen foam and for degenerating another part of the collagen foam to a collagen gel, comprising:
- a fractionizing channel comprising an inlet for receiving a flow of collagen foam, an outlet for a part of the flow of collagen foam, and a bottom portion which is inclined downwards in the direction of the flow of collagen foam,
- at least one outlet for collagen gel at the bottom portion of the fractionizing channel, wherein the position of the outlet is movable in a vertical direction at an end of the fractionizing channel.

In a fourth aspect, the present invention provides an elongated collagen sponge having a through-going hole or bore and a flexible wall. In a preferred embodiment, such a collagen sponge may be used for closing wounds or re-establishing gastrointestinal funnel and trachea walls in mammalians. Thus, the collagen sponge may have a circular or elliptical cross-section. The collagen sponge may be applied both as a filling, or as in a gastrointestinal funnel, or as an outer sleeve applied to an outer surface of a gastrointestinal funnel.

The inner diameter of the through-going hole or bore may, for application in various human gastrointestinal funnels and trachea, for example be as follows:

| | |
|---|---|
| Bowels: | 0.5–6 cm |
| Rectum: | 1–4 cm |
| Large intestine: | 2–6 cm |
| Small intestine: | 0.5–3 cm |
| Oesophagus: | 0.5–2 cm |
| Trachea: | 1–4 cm |

The collagen sponge may, e.g., be used for closing wounds after surgical removal of outpouchings on gastrointestinal funnel walls, such as after rectal surgery, such as after surgical removal of hemorrhoids. Examples of indications made possible by the collagen sponge according to the invention are:
- wound dressing,
- support of hemostasis, such as
  - weak, diffuse bleeding from parenchymatic organs,
  - surgical procedures on surgery locations where ectrosurgery or ligation has been performed prior to application of the collagen sponge,
  - prevention of rebleeding (securing of sutures),
  - application on burns,
  - bandage on topical injuries,
- drug delivery, such as delivery of antibiotics.

DESCRIPTION OF THE DRAWINGS

Figure 1:
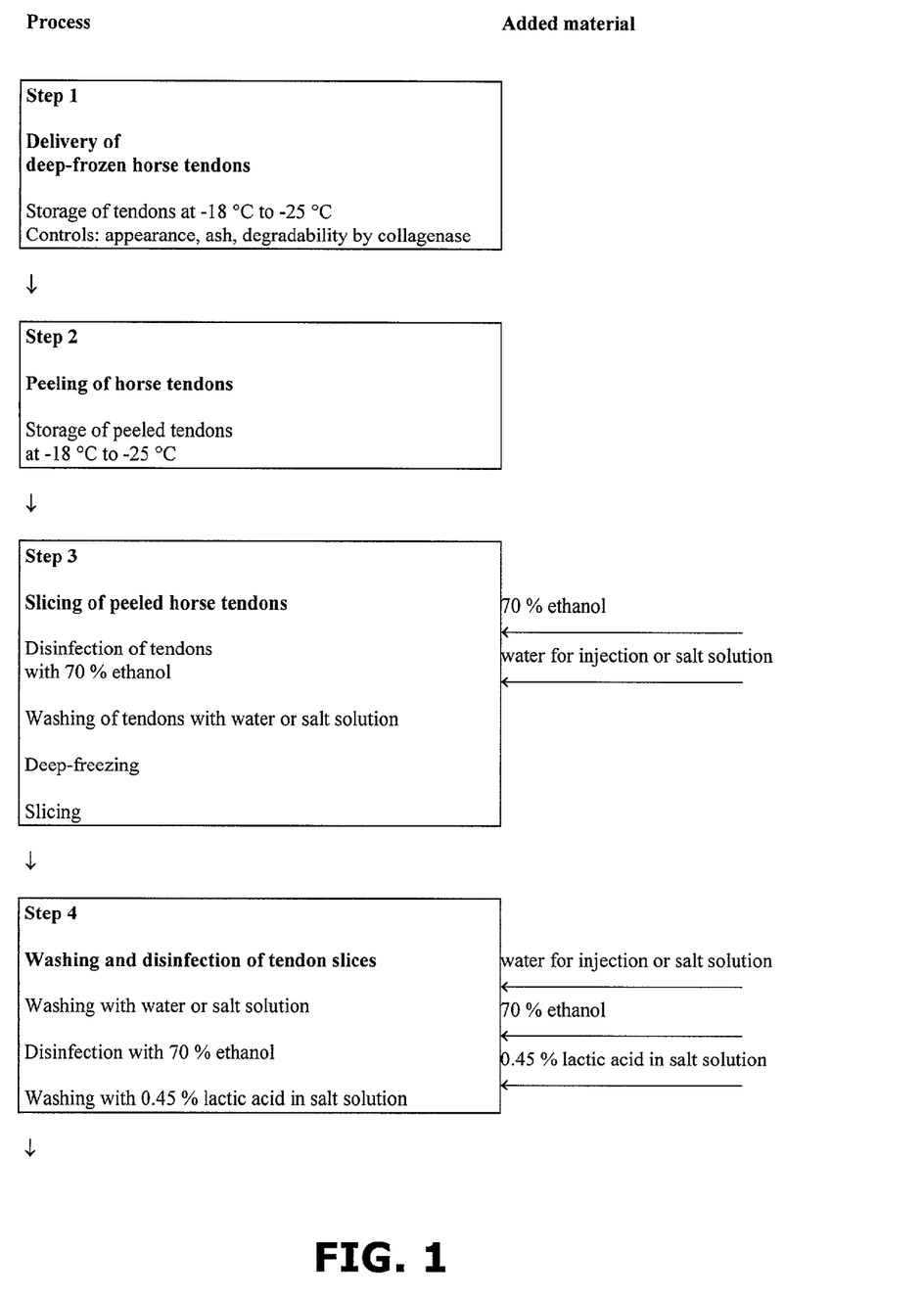
FIGS. 1 and 2 contain a flow chart illustrating the steps involved in a preferred embodiment of the method according to the invention.
Figure 2:
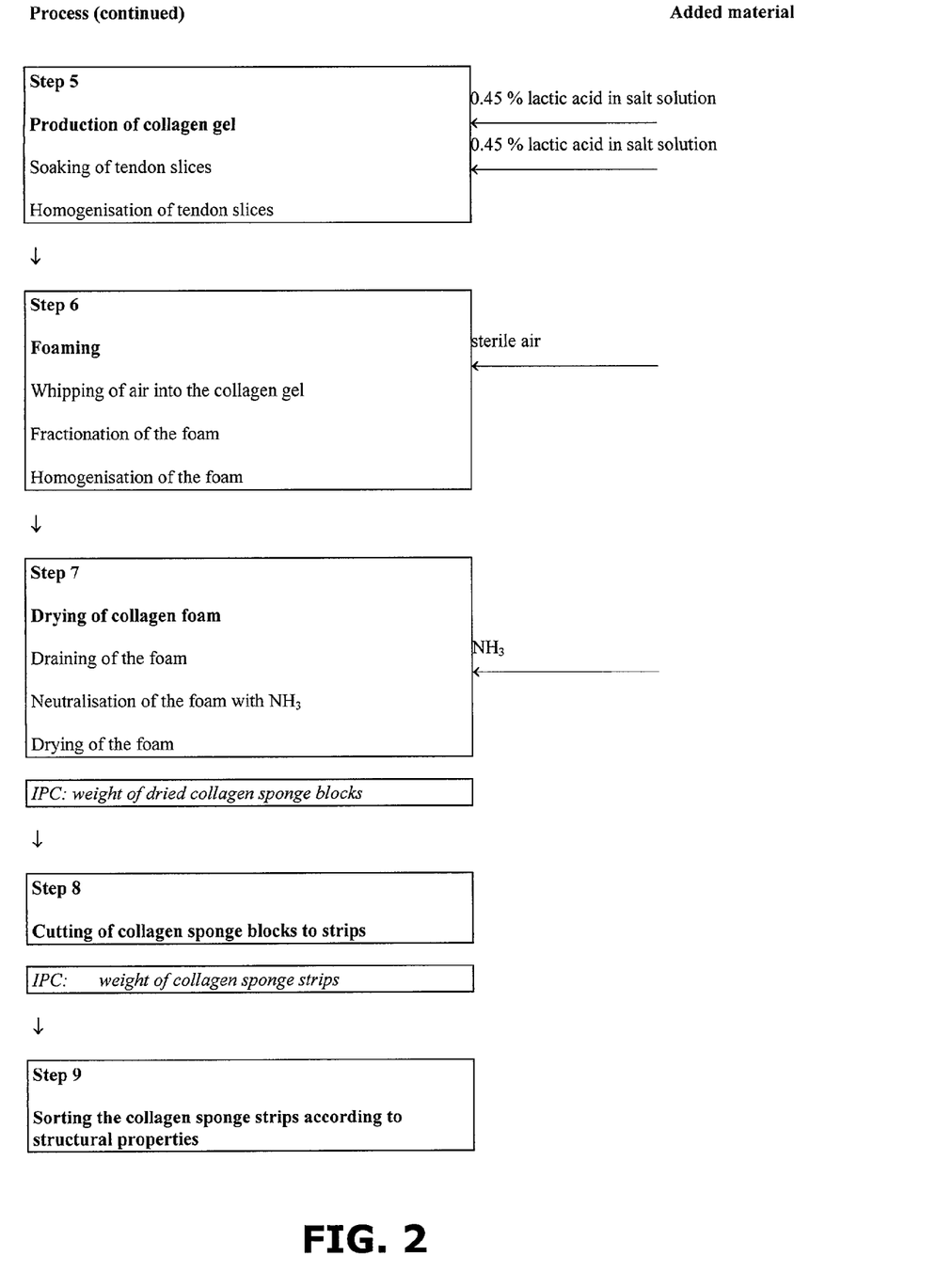

In a preferred embodiment, the invention comprises the following steps as illustrated in FIGS. 1 and 2:

Step 1 Delivery of Deep-Frozen Horse Tendons

The horse tendons are delivered and stored at −18° C. to −25° C.

Step 2 Peeling of Horse Tendons

In a half-frozen state, the thin skin of the tendons is manually or mechanically removed with a knife. The tendons are then again deep-frozen at −18° C. to −25° C.

Step 3 Mechanical Slicing of Peeled Horse Tendons

Optionally, peeled frozen tendons are disinfected for 30 min in 70% ethanol and passed into production rooms under ethanol. The tendons are then washed, and after washing the tendons are compacted to blocks and deep frozen at −18° C. to −25° C. The frozen tendon blocks are then sliced with a cutting machine with a rotating knife into slices having a thickness of approximately 1 mm.

Step 4 Washing and Disinfection of the Tendon Slices

In order to remove soluble proteins, the tendon slices are first soaked in water for injection for 3–6 hours, then washed with water for injection or demineralized water or salt solutions containing $Ca^{2+}$ and/or $Mg^{2+}$-ion within the range of 1–10 mM until the supernatant is free of hemoglobin. The tendon slices are then disinfected in 70% ethanol for 15 min and washed twice in 0.45% lactic acid in drinking water (sterile filtered and depyrogenized) to remove the ethanol.

Step 5 Production of Collagen Gel

The washed tendon slices are soaked in 0.45% lactic acid for 2–5 days, preferably 4 days, and then homogenized to a collagen gel. Exposure to 0.45% lactic acid is considered to be one of the main virus inactivation steps.

Step 6 Foaming

With dissolver stirrers sterile filtered air is whipped into the collagen gel. The arising foam is fractioned, and the fraction with a bubble size of 1–3 mm is collected. The foam is poured from the steel container into a barrel which is slowly rotated for approximately 3 minutes to obtain a homogeneous foam. This foam is filled into drying containers. The base of the container consists of a textile tissue which is permeable to fluids, so as to allow draining of the foam. After 5–24 hours, preferably 18–24 hours, the drained foam is exposed to ammonia gas e.g generated from a 26% ammonia solution of DAB quality. During this process, the surplus of ammonia shifts the pH of the foam to the alkaline region. Ammonia is removed during the subsequent drying process resulting in a neutral product.

Step 7 Drying the Foam

The foam is dried in warm air in a high grade steel drying chamber for 48–150 hours, preferably 120–150 hours. The result is collagen sponge shaped in blocks.

Step 8 Cutting the Collagen Blocks

Blocks, also referred to as sheets, of collagen may for example be used as carriers for a coating. The cutting is performed with a vertical cutting machine. First, the sides of the block are cut off to yield a block with vertical sides with a side length of 50 cm. This block is then cut vertically into 4 bars with a width of 11 cm. The bars are again trimmed at their upper and their lower side and then sliced into strips with dimensions of 50×11×0.4–0.7 cm. The weight of the collagen sponge strips preferably takes into account any specification of collagen in the final product to be achieved, such as hemostatic collagen sponges of the trademarks TACHOCOMB® H, TACHOCOMB® and TACHOTOP®.

Step 9 Sorting the Collagen Sponge Strips

The collagen sponge strips are then subjected to a visual control. Strips with one or more of the following defects are discarded:
- strips with an average chamber diameter smaller than 1 mm or larger than 3 mm
- strips with inhomogeneous chamber structure
- strips with holes (single chambers with a depth larger than the thickness of the sponge)

The sorted strips are stored for maximally 1 year in disinfected light metal containers at a temperature of 15–25° C.

Figure 3:
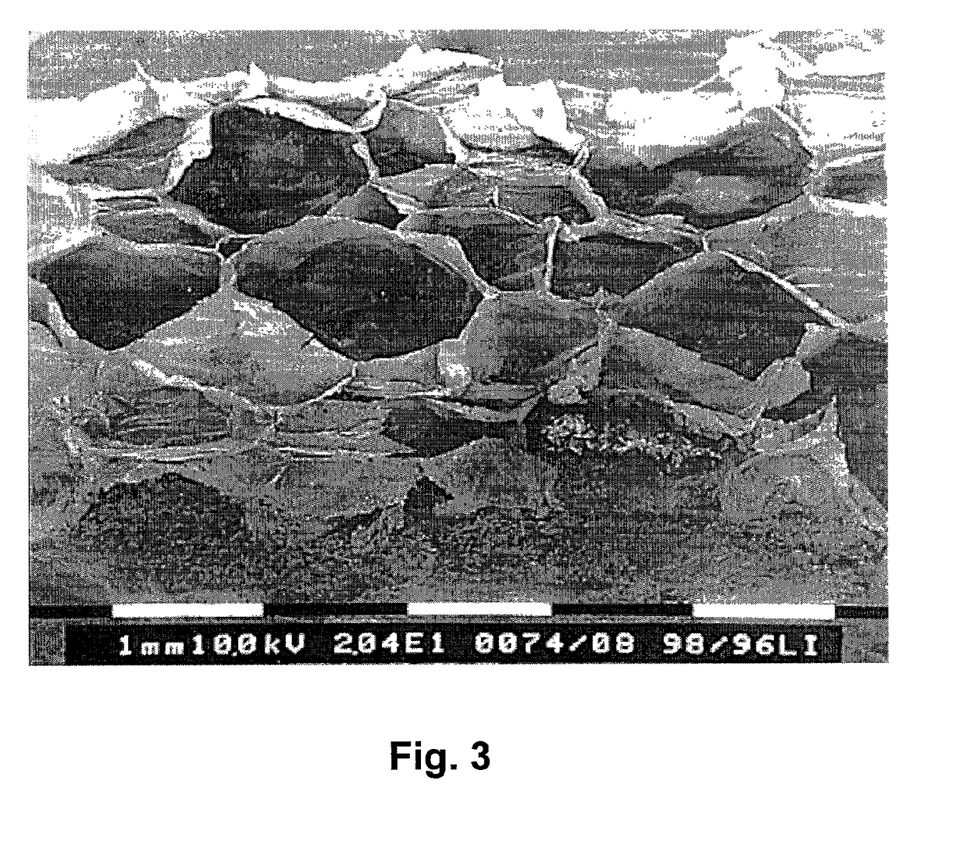
FIG. 3 is a photograph of the surface of a collagen sponge produced by a method according to the invention (courtesy Prof. Dr. Roman Carbon, Chirurgische Univ. Klinik Erlangen, Germany), and FIG. 4 discloses a stirring device for obtaining a measure of the viscosity of a collagen gel.

FIG. 3 is a photograph of the surface of a collagen sponge produced by a method according to the invention, the photograph being taken at a magnification factor of approximately 20,000 (courtesy Prof. Dr. Roman Carbon, Chirurgische Univ. Klinik Erlangen, Germany). The surface shown in the photography of FIG. 3 is a surface of a cross-sectional cut in a collagen sponge prepared by a method according to the present invention. The dark areas in the photograph represent chambers, while the light areas in the photography represent collagen material, including walls of collagen material separating the chambers.

Figure 4:
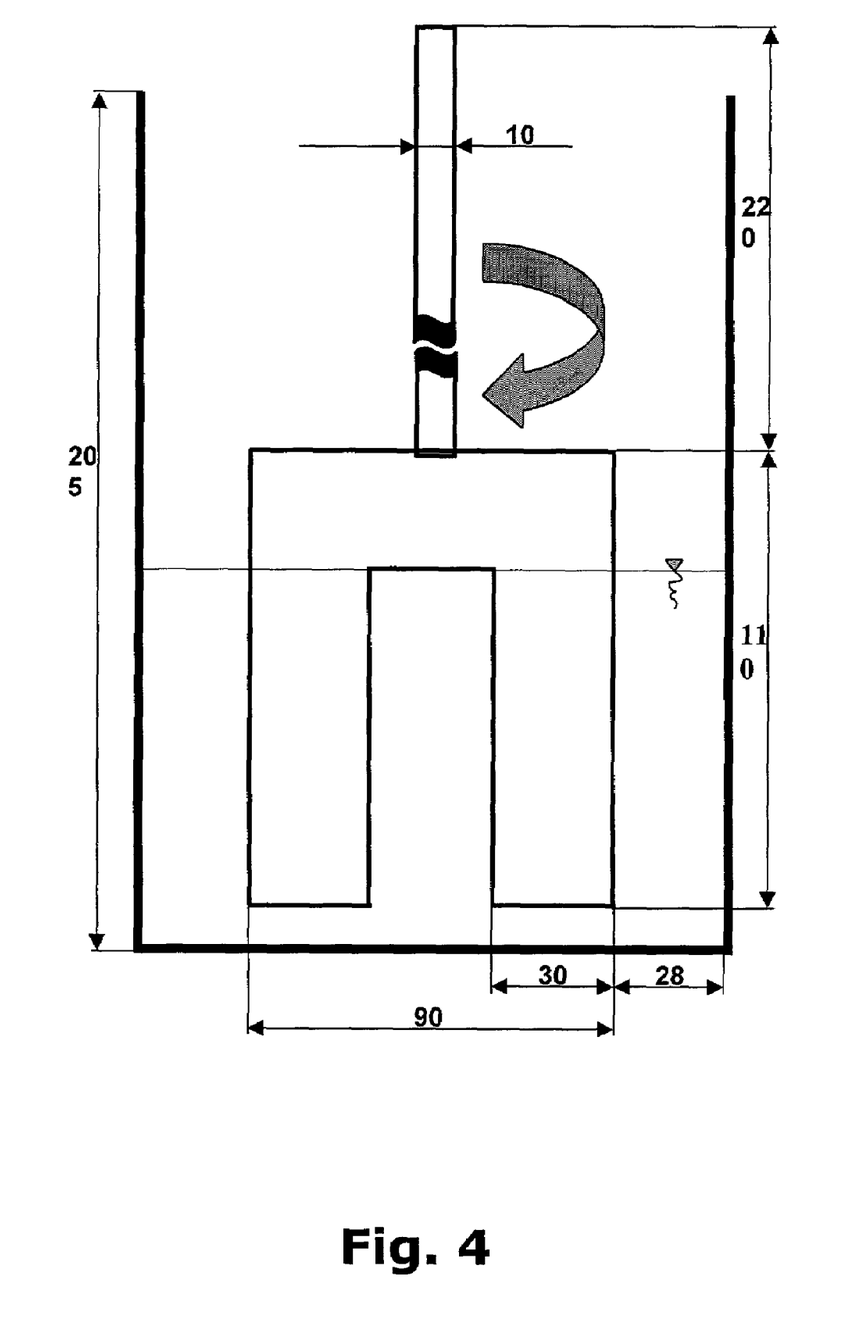

FIG. 4 shows a stirring device for obtaining a measure of a viscosity of a liquid, comprising a container adapted to accommodate a liquid and means for stirring the liquid. The stirring means comprise a rod attached to a fork shaped element. A liquid in the container is stirred by applying a torque to the rod, resulting in a rotational movement of the fork shaped element. The fork shaped element comprises a primary part to which the rod is attached and a first and a second secondary part. The secondary parts are attached to the ends of the primary part. As the fork shaped element rotates the surfaces moves the liquid and thus stirs the liquid.

In one embodiment the device has the following dimensions. The container is 110 mm high and 146 mm wide. The rod is 220 mm high and has a diameter of 10 mm. The primary part of the fork is 90 mm long and 30 mm high. The secondary parts are 90 mm high and 30 mm wide. The distance from an outer edge of the secondary parts to an inner surface of the container is 28 mm.

EXAMPLE I

Table I below shows parameter values of three different cycles of the method according to the invention.

TABLE I

|  | Cycle 1 | Cycle 2 | Cycle 3 |
| --- | --- | --- | --- |
| Peeling of tendons: waste (%) | 24 | 40 | 38 |
| Bioburden before peeling CFU/g tendon | $7 \times 10^4$ | $2.4 \times 10^5$ | $5 \times 10^5$ |
| Bioburden after peeling (CFU/g tendon) | — | $2 \times 10^3$ | $5 \times 10^3$ |
| Tendon weight per batch | 12.00 kg | 10.5 kg | 10.5 kg |
| Washing of peeled tendons with demineralized water | 30 min | 30 min | 30 min |
| Removal of soluble protein: washing of sliced tendons with demineralized water until washing solution is free of hemoglobin | 5 h | 5 h | 1.5 h |
| Disinfection with 70% ethanol | 15 min | 15 min | 15 min |
| Washing in 0.45% lactic acid | 21 min | 21 min | 21 min |
| Soaking in 0.45% lactic acid | 144 h | 120 h | 120 h |
| Homogenization- | Condux tooth mill | Condux tooth mill | Condux tooth mill |
| Gel viscosity (torque) | 6.9–7.8 Ncm | 6.9–7.8 Ncm | 7.1–9.5 Ncm |
| Dry mass of collagen gel | 6.3–8.3 mg/g | 8.9–9.4 mg/g | 7.8–9.4 mg/g |
| Foaming time per block | 37–47 min | 51–58 min | 54–62 min |
| Bioburden (CFU/ml wet foam) | — | 2 | 1 |
| Draining period | 18.5 h | 22 h | 18 h |
| Neutralization period | 24 h | 24 h | 24.5 h |
| Drying period | 147 h | 148.5 h | 144.5 h |
| Weight per block | 200–256 g | 195–228 g | 177–257 g |
| Bioburden of collagen sponge strips (CFU/g) | 14–1000 | <18–124 | <11–33 |
| Yield of collagen sponge strips: Length: 110 mm Width: 500 mm Height: 4–7 mm Weight: 770–1500 mg/strip | 405 | 379 | 433 |

Table II below shows parameter values of three different collagen sponges obtained by the method according to the invention.

TABLE II

|  | Sponge I | Sponge II | Sponge III |
| --- | --- | --- | --- |
| pH value (spec: 4–6) | 5.4 | 5.1 | 5.4 |
| Lactic acid content | 2.6% | 2.8% | 2% |
| Ammonium content | 0.2% | 0.2% | 0.1% |
| Soluble protein content | 0.1% | 0.05% | 0.08% |

TABLE II-continued

| | | | |
|---|---|---|---|
| Sulphate ashes content | 0.4% | 0.3% | 0.3% |
| Microbiological purity (CFU/g) | 14–1000 | <18–124 | <11–33 |
| Collagen content related to dry mass | 95% | 95% | 98% |
| Water content | 14% | 15% | 16% |
| Elasticity module | 10–45 N/cm$^2$ | 15–50 N/cm$^2$ | 12.3–41.0 N/cm$^2$ |
| Chamber size (diameter; mean value) | 2.3 mm | 2.1 mm | 2.9 mm |
| Density | 2.5–6.1 mg/cm$^3$ | 2.9–5.9 mg/cm$^3$ | 2.4-5.0 mg/cm$^3$ |

| | Sponge IV | Sponge V |
|---|---|---|
| pH value | 5.3 | 5.7 |
| Lactic acid content | 2.3% | 1.1% |
| Ammonium content | 0.1% | 0.1% |
| Soluble protein content | 0.04% | 0.11% |
| Sulphate ashes content | 0.3% | 0.2% |
| Heavy metal content | <20 ppm | <20 ppm |
| Microbiological purity | <12–345 CFU/g | <15–48 CFU/g |
| Collagen content related to dry mass | 95% | 96% |
| Water content | 14% | 12% |
| Elasticity module | 10.4–42.1 N/cm$^2$ | 20–47 N/cm$^2$ |
| Chamber size (diameter; mean value) | 2.9 mm | 2.5 mm |
| Density | 2.9–5.3 mg/cm$^3$ | 2–6.8 mg/cm$^3$ |

EXAMPLE II

This example relates to the indirect measurement of the viscosity of the collagen gel by torque measurement. The equipment used for the torque measurement is:

Stirring machine: EUROSTAR POWER control-visc
Windows-Software: IKASOFT dc
Torque indicator: VISCOKLICK VK 1
Datalogger DC 2
Special stirrer construction ("fork") with defined dimensions, cf. FIG. 4
Funnel with an inner diameter of 14.6 cm and a height of 20.5 cm
Thermometer
Balance An amount of 1500 g of collagen gel is filled into the funnel. The temperature of the sample is 23° C. The "fork" stirrer is fixed in the center of the funnel. Then measurement is started. The Torque indicator is transforming the resistance of the stirrer into a value (Ncm) representing the dynamic gel viscosity.

In order to verify the measurement of the torque, a standard solution of 59% Polyethylenglycol is prepared. Viscosity of this solution is measured by a Haake Visosimeter RV 20 Rotovisko. The dynamical viscosity η of this solution is in the range of η=925±25 mPas at 23° C. This solution viscosity is measured by the above gel measuring equipment, and the torque value thereby measured should be in the range of 3.66 Ncm±5% at 23° C.

REFERENCES

Baer, E. Gathercole, L. J. and Keller, A., *Structure hierarchies in tendon collagen: an interim summary*, Proc. Colston Conf., 1974, 189; Hiltner, A. Cassidy, J. J. and Baer, E., *Mechanical properties of biological polymers*, Ann. Rev. Mater. Sci., 15, 455, 1985)

The invention claimed is:

1. A method of preparing a collagen sponge, comprising:
preparing a collagen gel,
mixing air into the collagen gel, so as to obtain a collagen foam,
drying the collagen foam, so as to obtain a dry block of collagen sponge having a three-dimensional structure with stacked chambers which are separated and substantially totally enclosed by walls of collagen material,
isolating, from the block of collagen sponge, parts of sponge showing at least one of:
a chamber diameter of more than 0.75 mm or less than 4 mm, and
an average chamber diagonal dimension of 3 mm.

2. A method according to claim 1, wherein the collagen gel has a dynamic viscosity of 2–20 Ncm.

3. A method according to claim 1, further comprising, subsequent to said mixing air into the collagen gel, homogenizing the collagen foam for a period of 2 to 4 minutes.

4. A method according to claim 1, wherein said drying comprises drying at a temperature between 15° C. and 40° C. for a period of 100–200 hours.

5. A method according to claim 1, wherein the collagen sponge fulfils at least one of the following criteria:
pH-value between 5.0 and 6.0,
lactic acid content at the most 5%,
ammonium content at the most 0.5%,
soluble protein content, calculated as albumin content, at the most 0.5%,
sulphate ashes content at the most 1.0%,
heavy metal content at the most 20 ppm,
microbiological purity, at the most $10^3$ CFU/g,
collagen content of 75 to 100%,
density of 1 to 10 mg/cm$^3$,
elasticity module in the range of 5–100 N/cm$^2$.

6. A method according to claim 1, wherein the collagen sponge has a water content of not more than 20%.

7. A method according to claim 1, wherein said isolating parts of collagen sponge comprises dividing the collagen sponge into a plurality of parts by cutting.

8. A method according to claim 1, wherein said drying comprises drying at a temperature between 15° C. and 60° C. for a period of 48–200 hours, so as to obtain a dry collagen sponge.

9. A method according to claim 8, wherein said drying is carried out at a pressure of 700 to 900 mbar.

10. A method according to claim 1, further comprising, prior to said drying the collagen foam and subsequent to said mixing air into the collagen gel, adding a neutralizer to the collagen foam and neutralizing the collagen foam in order to achieve a pH-value in the collagen foam between 6.5 and 8.5.

11. A method according to claim 10, wherein the neutralizer comprises an ammonia solution.

12. A method according to claim 10, wherein the collagen foam is neutralized for a period of 5–30 hours.

13. A method according to claim 12, wherein the collagen foam is neutralized for a period of 20–30 hours.

14. A method according to claim 1, wherein said mixing air into the collagen gel comprises:
   mixing ambient air into the gel with a mixer so as to generate a collagen foam,
   feeding the mixed gel foam into a fractionizing channel, and
   separating collagen gel and collagen foam contained in the fractionizing channel.

15. A method according to claim 14, wherein said separating collagen gel and collagen foam comprises:
   separating a selected part of the collagen foam contained in the fractionizing fractionising channel, and
   leading the selected part of the collagen foam out of the fractionizing channel for drying thereof.

16. A method according to claim 14, further comprising maintaining a temperature between 15° C. and 40° C. in the fractionizing channel.

17. A method according to claim 14, wherein at least some of the collagen gel separated from the collagen foam in the fractionizing channel is led back to the mixer.

18. A method according to claim 17, wherein the ratio between the amount of collagen gel which is led back to the mixer from the fractionizing channel and the amount of fresh collagen gel led to the mixer is between 0.1 and 0.5.

19. A method according to claim 1, wherein the collagen content of the isolated parts of sponge is 50 to 100%.

20. A method according to claim 19, wherein the collagen gel comprises collagen material of different types from at least one of the following sources: mammalian, transgenic and recombinant sources.

21. A method according to claim 20, wherein the collagen comprises material from tendons selected from the group consisting of equine tendons, bovine tendons and human tendons.

22. A method according to claim 21, wherein said preparing the collagen gel comprises:
   storing the tendons at a temperature between −10° C. and −30° C., and peeling the tendons,
   removing foreign protein from the tendons,
   reducing germ content in the tendons,
   swelling the tendons,
   homogenizing the swelled tendons.

23. A method according to claim 22, wherein said swelling the tendons comprises adding lactic acid to the tendons.

24. A method according to claim 22, wherein said homogenizing the swelled tendons comprises obtaining a substance comprising particles of tendons, the particles having a length or diameter of 0.8 to 1.2 cm.

25. A method according to claim 22, wherein said homogenizing the swelled tendons comprises obtaining a substance having a viscosity of 2 to 20 Ncm.

26. A method according to claim 22, wherein said homogenizing the swelled tendons is carried out by means of a toothed disk mill.

27. A method according to claim 22, wherein said swelling the tendons comprises storing the tendons at a temperature of 4° C. to 25° C. for a period of 48 to 200 hours.

28. A method according to claim 27, wherein the tendons are stored for a period of 100 to 120 hours.

29. A method according to claim 22, wherein said reducing germ content comprises adding an acid and an organic solvent to the tendons.

30. A method according to claim 29, wherein the organic solvent is an alcohol.

31. A method according to claim 30, wherein the alcohol is ethanol.

32. A method according to claim 29, wherein the acid is an organic acid.

33. A method according to claim 32, wherein the organic acid is lactic acid.

34. A method according to claim 33, wherein the lactic acid is a 0.45% lactic acid.

35. A method according to claim 32, wherein the acid has a pH value in the range of 1 to 4.

36. A method according to claim 35, wherein the acid has a pH value in the range of 1.5 to 3.5.

37. A method according to claim 36, wherein the acid has a pH value in the range of 2.5 to 3.0.

38. A method of preparing a collagen sponge, comprising:
   preparing a collagen gel,
   mixing air into the collagen gel, so as to obtain a collagen foam,
   drying the collagen foam, so as to obtain a dry block of collagen sponge having a three-dimensional structure with stacked chambers which are separated and substantially totally enclosed by walls of collagen material,
   isolating, from the block of collagen sponge, parts of sponge having the following properties:
   elasticity module in the range of 5 to 100 N/cm$^2$,
   density in the range of 1 to 10 mg/cm$^3$,
   and at least one of:
   chamber diameter of more than 0.75 mm and less than 4 mm, and
   a chamber diameter average of at most 3 mm.

* * * * *